United States Patent [19]
Farber

[11] Patent Number: 5,765,437
[45] Date of Patent: Jun. 16, 1998

[54] COMPOST AERATOR AND MONITOR

[76] Inventor: Paul A. Farber, 3948 S. 2075 West, Roy, Utah 84067

[21] Appl. No.: 673,507

[22] Filed: Jul. 1, 1996

[51] Int. Cl.$^6$ .................................................. G01N 1/08
[52] U.S. Cl. ................. 73/864.43; 408/1 R; 408/210; 408/230
[58] Field of Search .................. 73/864.43; 172/371; 175/394; 408/1 R, 1 BD, 210, 230

[56] References Cited

U.S. PATENT DOCUMENTS

| | | | |
|---|---|---|---|
| 168,890 | 10/1875 | Field | 52/157 |
| 200,489 | 2/1878 | Tweed | 52/157 |
| 601,124 | 3/1898 | Cole | 454/174 |
| 728,609 | 5/1903 | Pitcher | 52/153 |
| 1,927,871 | 9/1933 | Irwin et al. | 73/864.43 |
| 2,435,608 | 2/1948 | Sanford et al. | 73/864.43 |
| 2,666,623 | 1/1954 | Johnson | 175/18 |
| 3,847,023 | 11/1974 | Mallander et al. | 73/864.43 |
| 5,405,780 | 4/1995 | Hamilton, Jr. | 435/290.2 |
| 5,449,254 | 9/1995 | Beckner | 408/1 R |

FOREIGN PATENT DOCUMENTS

| | | | |
|---|---|---|---|
| 152560 | 2/1951 | Australia | 73/864.43 |
| 257857 | 11/1965 | U.S.S.R. | 73/864.43 |
| 773473 | 10/1980 | U.S.S.R. | 73/864.43 |
| 1000828 | 2/1983 | U.S.S.R. | 73/864.43 |
| 243931 | 5/1989 | U.S.S.R. | 73/864.43 |
| 1624309 | 1/1991 | U.S.S.R. | 73/864.43 |

OTHER PUBLICATIONS

*Patent Abstracts of Europe* "Device and method for making Compost" abstract of GB 2138795 dated Oct. 31, 1984 by Clifford Arthur Wilson.

Primary Examiner—Thomas P. Noland
Attorney, Agent, or Firm—Thompson E. Fehr

[57] ABSTRACT

A compost aerator and monitor which has a cylindrical helical screw, preferably with a sharpened first end. The diameter of the cylindrical helix and the tightness of the windings are selected so as, when the screw is inserted into a compost pile, to create a core of compost material that is sufficiently large to be cohesive and representative but not so large that the weight of the core will cause the core to fall from the screw when such screw is withdrawn from the compost pile. Attached to the second end of the screw is a handle with sufficient leverage to enable the screw to be turned rapidly and, consequently, rapidly introduced into a compost pile and to preclude the screw from rotating as the screw is withdrawn from the pile, thereby retaining the core of compost material. Optionally, either a traditional brace or a traditional power drill can replace the simple handle; and a shaft can be inserted between the screw and the handle or the brace. The handle or brace may be either permanently or removably attached to the screw or the shaft, while the power drill is removably connected to the screw or the shaft.

27 Claims, 10 Drawing Sheets

COMPOST AERATOR AND MONITOR

BACKGROUND OF THE INVENTION

1. Field of the Invention

This invention relates to a device and method for aerating and monitoring the status of a compost pile.

2. Description of the Related Art

With increasing environmental awareness, more individuals and neighborhood associations are establishing compost piles as a responsible way to dispose of yard debris while creating organic fertilizer for gardening.

The desired biological changes in organic matter within a compost pile can be facilitated by the addition of more oxygen through aeration. Consequently, this is one purpose for the present invention. And decomposition will be even further accelerated by the increased penetration of moisture into the compost pile as a result of such aeration.

It can, furthermore, be helpful to know what is in the compost pile. Even if a single individual is responsible for the pile, that person may have a lapse of memory. When the pile is a communal effort, it becomes even more difficult to know the contents. Thus, an additional purpose for the present invention is to extract a core sample from the pile for examination. The stage of decomposition at the tested location can readily be observed; and tests can be conducted upon the sample to determine the ratio of carbon to nitrogen, acidity, bacterial count, etc. Additionally, by comparing samples extracted at different times, the rate of decomposition can be established.

Traditionally, aeration of a compost pile is accomplished with a pitchfork, spade, or the like. This process consists essentially of turning the material in the compost pile to mix air into such material. Because new material is generally added to the top of the compost pile, this technique has the disadvantage of contaminating the deeper, more thoroughly decomposed material with higher—and, therefore, less decomposed-material. The entire quantity of disturbed material must then be allowed to remain a sufficient length of time to permit adequate decomposition of the more recent material.

Moreover, utilizing a pitchfork, spade, or the like to extract a core sample for analysis is too laborious and imprecise. Again, even with reasonable care, material from different levels—and, therefore, different states of decay—will often be unintentionally mixed. And to minimize the likelihood of such mixing, considerable time and effort would have to be expended.

No device appears to have been patented for the aeration and monitoring of compost piles.

Six devices intended for entirely different purposes do, however, resemble the present invention.

U.S. Pat. No. 168,890 and U.S. Pat. No. 200,489 both describe and claim a picket-pin, i.e., a device which can be screwed into the ground securely to retain the rope from a tethered animal, such as a horse. The picket-pin of each patent consists of a handle attached to a spiral shaft. U.S. Pat. No. 168,890 merely asserts that the "shank . . . is bent in spiral form . . . ." U.S. Pat. No. 200,489 describes ". . . a spiral or screw having the general form of a corkscrew, which is made of a flat bar of steel or wrought-iron, having its greatest diameter at right angles to the axis of the screw. The bar is tapering, being thickest at the upper end of the screw, and gradually diminishing in thickness toward the lower end, upon which there is a chisel-edge. The object in tapering the bar is to cause it to wedge as it enters the earth, so as to form a solid bearing."

Not only is the function for the devices of these two patents to retain each device within the earth, but their claims and disclosures fail to provide the critical details of construction which would enable these devices to serve as compost aerators and monitors. An essential feature of the "spiral or screw" for a compost aerator and monitor is that it be wound in such a fashion as to create the shape of a hollow cylinder within the windings, i.e., the "spiral or screw" must be wound as a cylindrical helix, in order to create a space in which the compost will collect for subsequent withdrawal. Neither of these two prior patents, however, describes the dimensions of the central cylindrical cavity which exists between the windings. In fact, both such patents fail even to state that a central cylindrical cavity exists. And the related drawings seem to show that either there is no such cavity or that its diameter is so minimal as to preclude the collection of enough compost to create a cohesive, representative mass.

The claims and disclosures for these two patents, furthermore, do not appear to describe a head which would provide sufficient leverage conveniently to permit the rapid introduction of the devices into well-compacted compost or to preclude the devices from rotating as they are withdrawn, which would allow the escape of any compost that may have collected between the windings.

Similarly, the function of the guy anchor described and claimed in U.S. Pat. No. 728,609 is to retain the guy anchor within the earth; and the claims and disclosures of this patent fail to provide the critical details of construction which would enable the guy anchor to serve as a compost aerator and monitor. The guy anchor is intended to be screwed into the ground using a removable bar (or key). The relevant disclosure simply states, "The lower end of said body portion . . . consists of a piece of rounded metal . . . , which is formed into a screw, [sic] and by turning the upper body portion . . . the screw will force itself into the ground similar [sic] to that of a corkscrew." Again, this patent does not describe the dimensions of the central cylindrical cavity which exists between the windings and even fails to state that a central cylindrical cavity exists. The drawings do appear to show such a central cylindrical cavity, but such cavity seems to be so large and the windings appear to be so far apart that the weight of the compost material within the cavity would combine with a significant lack of structural support from the windings to cause such compost material to fall from the windings as the guy anchor is withdrawn from a compost pile.

Moreover, the removable design of the bar would cause it to slide and, therefore, be inconvenient for use in preventing rotation of the helical screw as the guy anchor is withdrawn from the compost. Additionally, the bar could easily be lost.

Another spirally shaped device is one element within the hay boring apparatus of U.S. Pat. No. 601,124. The hay boring apparatus has knives at a lower end of a tube, which knives move in a circle to cut into a pile of hay. This permits the tube to descend into the pile as the cut hay is removed by being transported upward through the tube as a result of the rotation of the spirally shaped device, termed a "wormer." Once again, no dimensions are given for the size of the central cylindrical cavity or the tightness of the windings. The drawings, however, appear to depict a cavity with such large dimensions and windings so far apart from one another that inadequate structural support would be provided to a central core of compost material to permit such core to be withdrawn without collapsing and thereby preventing the hay boring apparatus from successfully either aerating or monitoring a compost pile.

The ice boring device of U.S. Pat. No. 2,666,623 basically utilizes a cutting edge at the lower end of a helix. As the ice boring device is turned, the cutting edge goes deeper into the ice; and an annular ring of ice is forced up the helix, leaving a central core of uncut ice. The helix, thus, provides essentially no structural support for the central core. With ice this is unimportant; but were the ice boring device to be used in a compost pile, the core of compost material would collapse, precluding either aeration or monitoring of the compost pile.

Unlike the devices of the preceding patents, the auger included within the Apparatus for Batch Composting of Waste Material disclosed within U.S. Pat. No. 5,405,780 can aerate compost material; this auger cannot, however, monitor the material within a compost pile. Aeration is accomplished by rotation of the auger to raise materials from lower in the pile to the top and would, consequently, have the disadvantage of requiring the entire pile to be unavailable for use until the most recently added material had had sufficient time to reach the desired state of decomposition. Monitoring would be impossible because the disclosed auger has a shaft running longitudinally through the central cylindrical cavity formed by the windings of the auger, which shaft would preclude a core of compost material from accumulating within the cavity.

One apparently unpatented anchor—which is imported and marketed by Wal-Mart Stores, Inc. in the United States; which is made in Taiwan by the Yau Feng Chain Company; and which has no designation other than a Spiral Stake—does appear, however inadvertently, to have a screw of the appropriate shape and size to create the desired core of compost material. But this Spiral Stake does not have a head which would provide sufficient leverage conveniently to permit the rapid introduction of the device into well-compacted compost or to preclude the device from rotating as it is withdrawn. The compost which had collected between the windings after insertion into the compost pile would, therefore, be allowed to escape during the process of withdrawal from the compost pile.

SUMMARY OF THE INVENTION

The present Compost Aerator and Monitor has a cylindrical helical screw, preferably with a sharpened first end. The diameter of the cylindrical helix and the tightness of the windings are selected so as, when the screw is inserted into a compost pile, to create a core of compost material that is sufficiently large to be cohesive and representative but not so large that the weight of the core will cause the core to fall from the screw when such screw is withdrawn from the compost pile.

Attached to the second end of the screw is a handle with sufficient leverage to enable the screw to be turned rapidly and, consequently, pushed rapidly into a compost pile and to preclude the screw from rotating as the screw is withdrawn from the pile, thereby retaining the core of compost material. This core can then be inspected and analyzed to monitor the compost pile for, inter alia, the status of decomposition, the rate of decomposition, moisture, nature of the compost material, and location of any boundary between compost material which has decomposed sufficiently to be a final product, i.e., humus, and compost material which has not yet attained such a state of adequate decomposition. Removal of the core from the compost pile creates a channel for aeration as well as a pathway for moisture more rapidly to penetrate into the recesses of the pile.

As the screw penetrates deeper into the compost, the material from the upper layers is pushed from the screw so that there is no mixing from different layers and that the core sample is characteristic of the deepest layer into which the screw was inserted.

One may, if desired, remove the core sample from the area of the compost pile to preclude the mixing of that sample with the upper layer of the compost pile. More often, however, the core will simply be visually inspected while retained within the screw and the screw will be inserted again into the compost pile for further monitoring or aeration. Such re-insertion will then cause the core to be pushed from the screw and deposited on the top of the compost pile where the increased number of bacteria within the material from the core (because of the more advanced decomposition of such material as compared to the more newly added material on top of the compost pile) will serve to accelerate the decomposition of the more recently added material at the top of the compost pile.

DESCRIPTION OF THE PREFERRED EMBODIMENT

Figure 1:
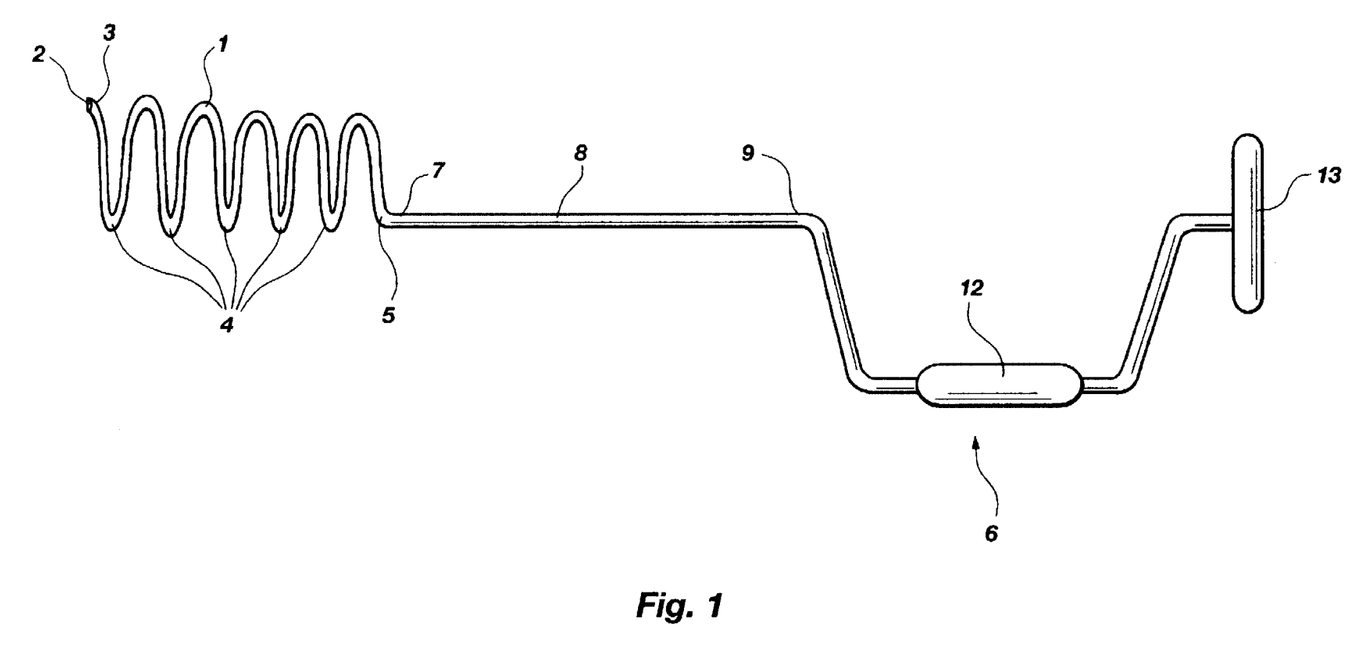
FIG. 1 depicts the preferred embodiment of the Compost Aerator and Monitor.
Figure 2:
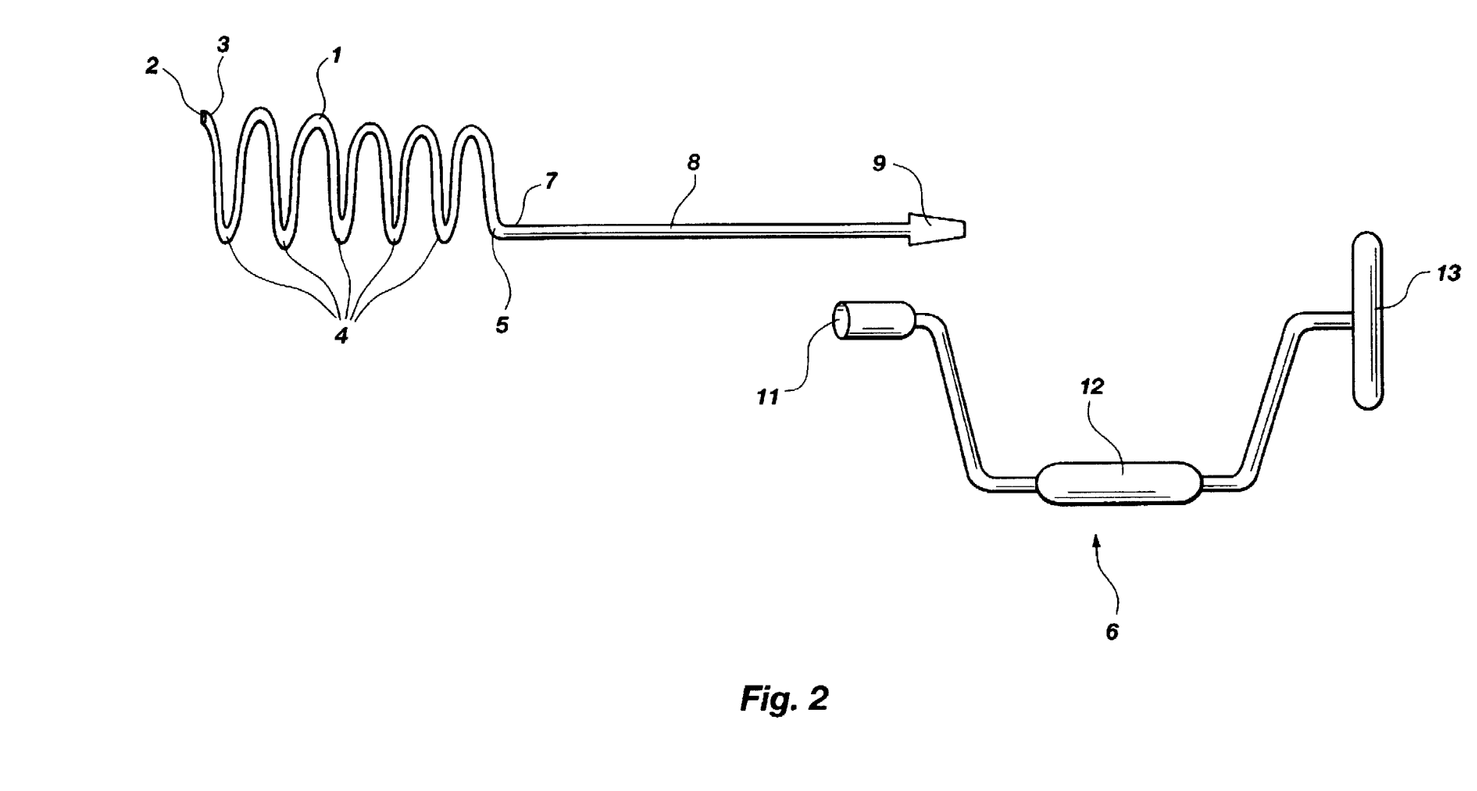
FIG. 2 shows an alternative embodiment wherein the shaft between the screw and the brace has its end which attaches to the brace formed into the traditional shape for removable insertion into the adjustable aperture of the brace.

The Compost Aerator and Monitor, as illustrated in FIG. 1, has a screw 1 shaped as a cylindrical helix, preferably with a sharpened tip 2, and even more preferably so sharpened as to have the same shape as the tip of a traditional chisel, at the first end 3 of the screw 1.

The diameter of the central cylindrical cavity formed by the cylindrical helix of the screw 1 and the tightness of the windings 4 of the screw 1 are of such sizes that, when the screw 1 is inserted into the compost pile, there is collected within the windings 4 of the screw 1 a core of compost material that is sufficiently large to be cohesive and representative but not so large that the weight of the core will cause the core to fall from the screw 1 when such screw 1 is withdrawn from the compost pile. It has been experimentally determined that, preferably, the screw 1 is ten inches long, the distance between similar points on adjacent windings 4 is two inches, and the diameter of the central cylindrical cavity is one inch.

Although the second end 5 of the screw 1 can be connected directly to a traditional brace 6, the second end 5 of the screw 1 is preferably connected to a first end 7 of a straight shaft 8. The second end 9 of the shaft 8 is attached to the traditional brace 6.

Figure 3:
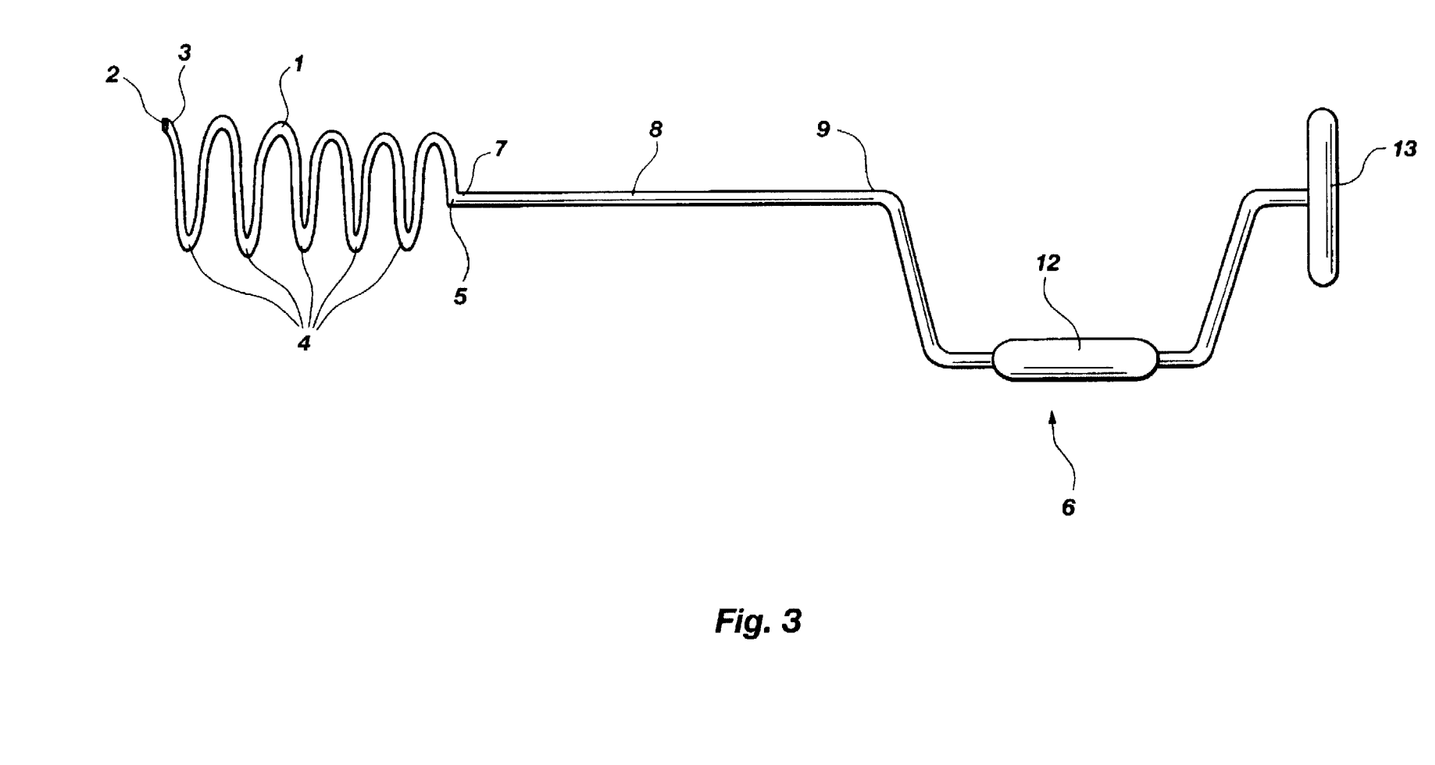
FIG. 3 displays an alternative embodiment in which the shaft is aligned with the center of the central cylindrical cavity formed by the windings of the screw.
Figure 4:
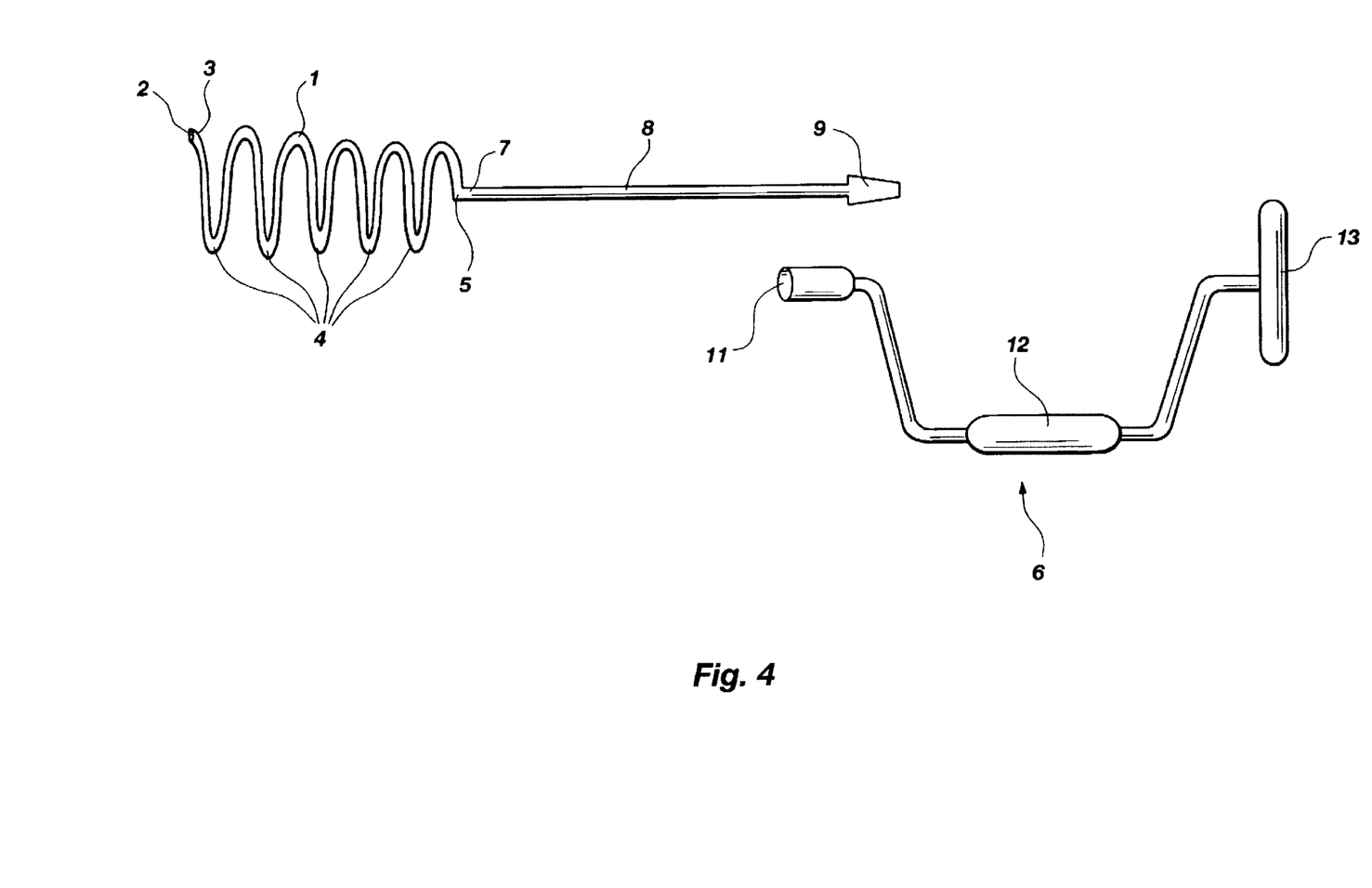
FIG. 4 is a modification of the embodiment from FIG. 3 wherein the shaft between the screw and the brace has its end which attaches to the brace formed into the traditional shape for removable insertion into the adjustable aperture of the brace.

Preferably, as shown in FIG. 1, the shaft 8 is aligned with the circumference of the central cylindrical cavity formed by the cylindrical helix of the screw 1. Alternatively, the shaft 8 may be aligned with any other point, such as the center of the central cylindrical cavity formed by the cylindrical helix of the screw 1, as depicted in FIG. 3.

Figure 5:
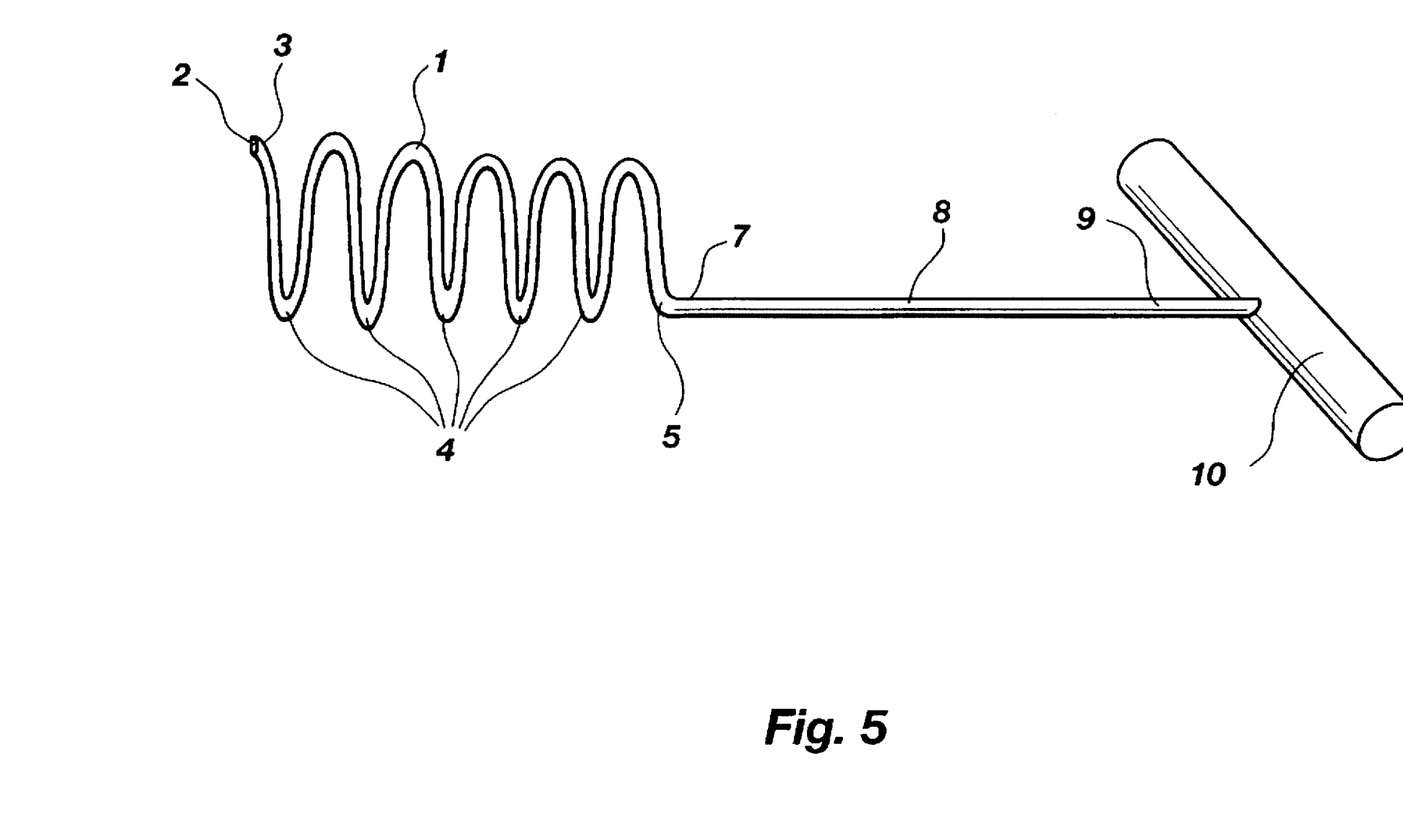
FIG. 5 illustrates an alternative embodiment of the embodiment from FIG. 1 in which alternative the brace has been replaced with a straight handle.
Figure 6:
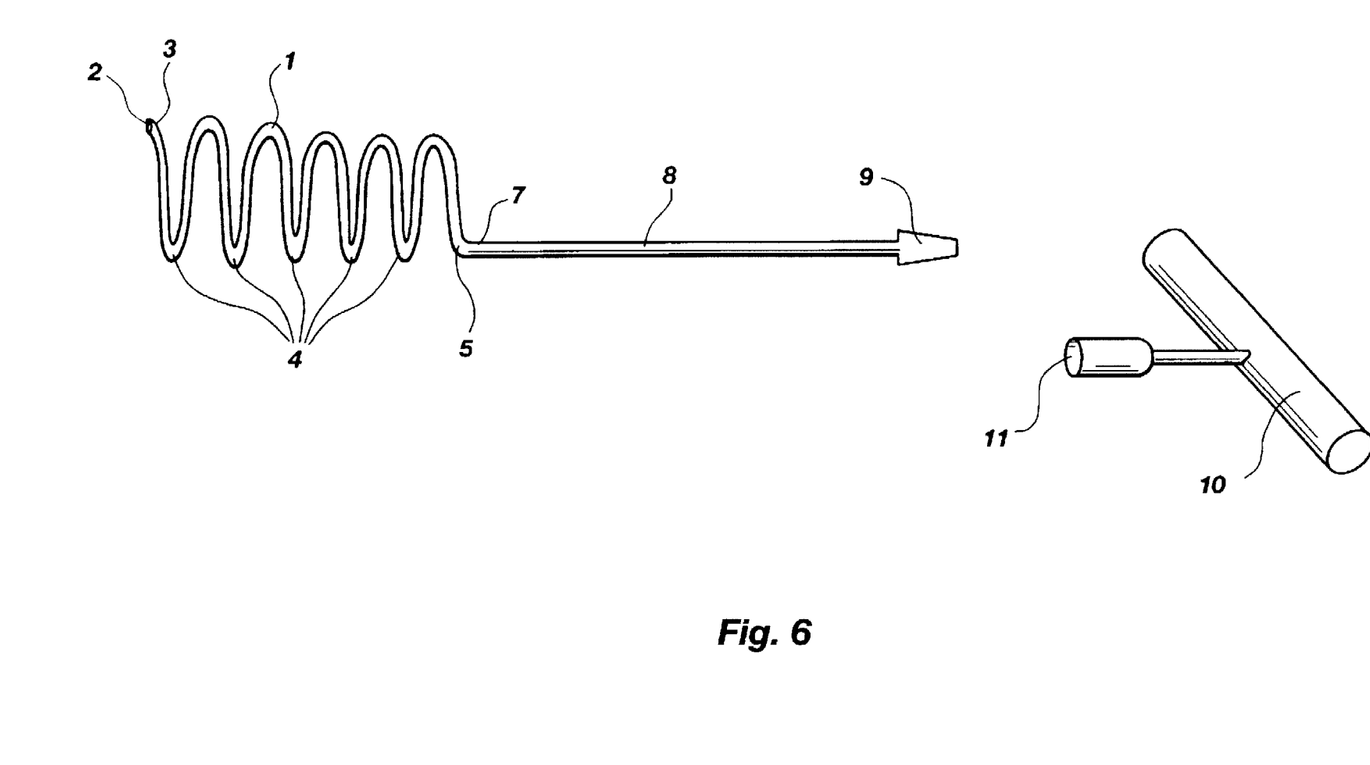
FIG. 6 displays a modification of the embodiment from FIG. 5 wherein the shaft between the screw and the brace has its end which attaches to the brace formed into the traditional shape for removable insertion into the adjustable aperture of the brace.
Figure 7:
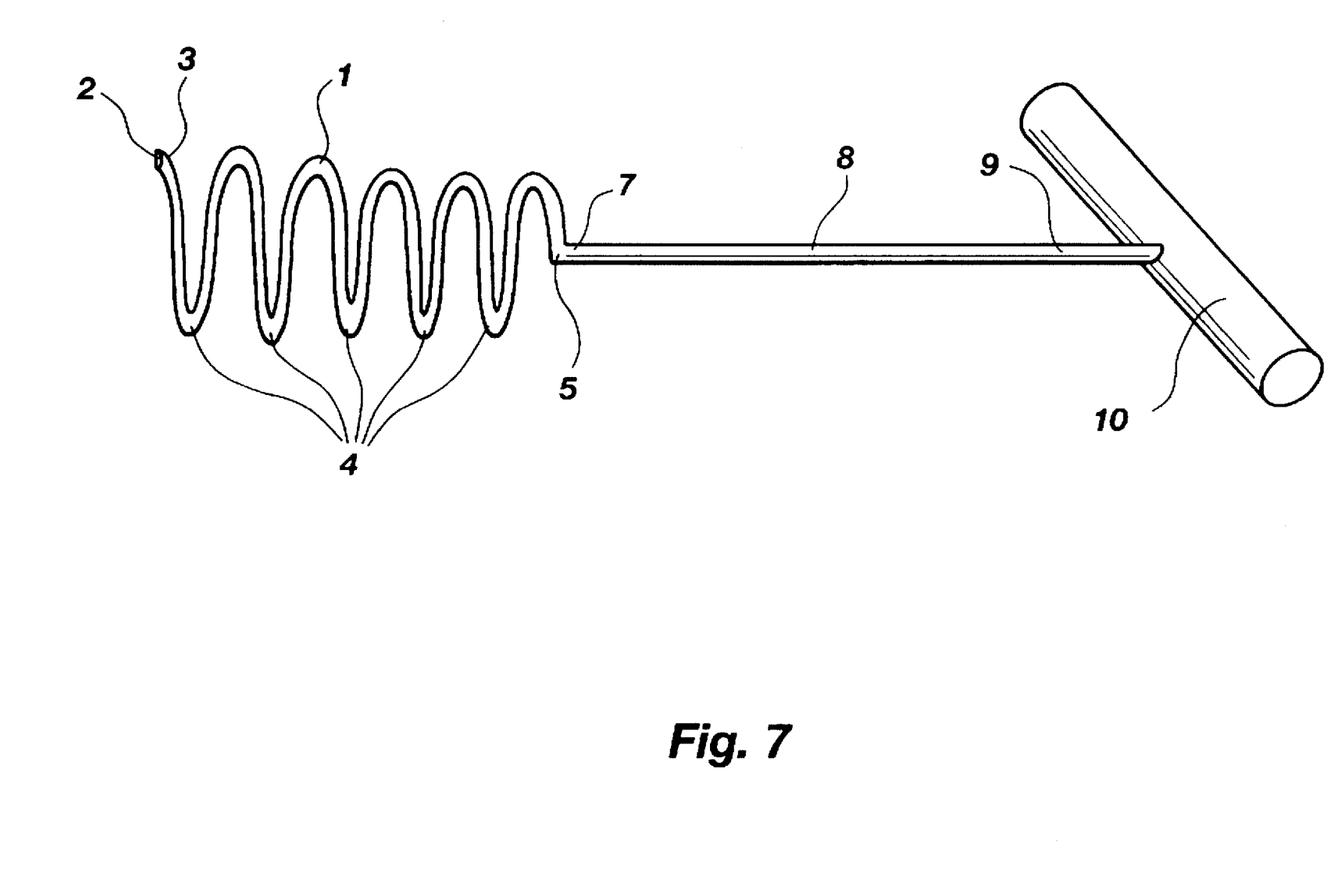
FIG. 7 shows an additional alternative embodiment of the embodiment from FIG. 5 in which the shaft is aligned with the center of the central cylindrical cavity formed by the windings of the screw.
Figure 8:
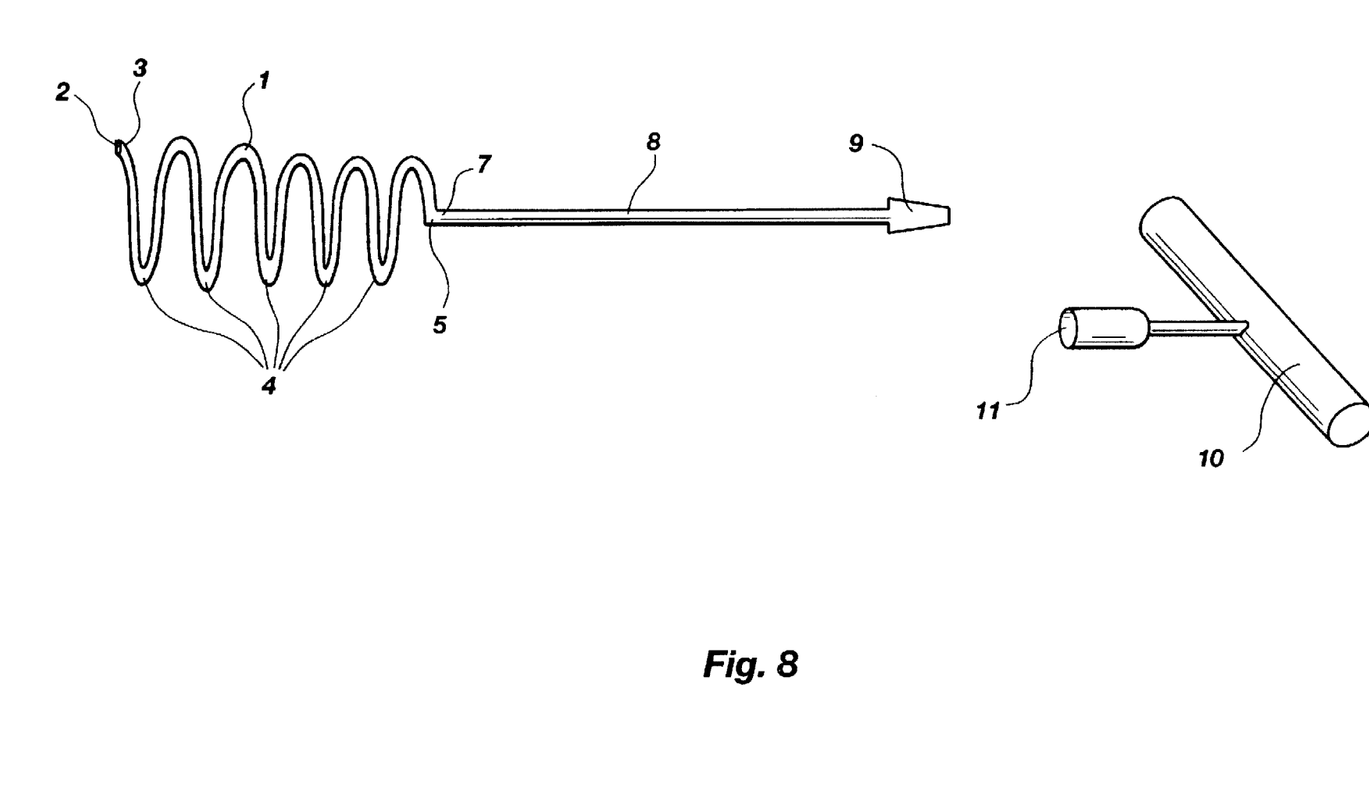
FIG. 8 portrays a modification of the embodiment from FIG. 7 wherein the shaft between the screw and the brace has its end which attaches to the brace formed into the traditional shape for removable insertion into the adjustable aperture of the brace.

Rather than utilizing the traditional brace 6, a simple handle 10 can be attached to the second end 9 of the shaft 8, as illustrated in FIG. 5 and FIG. 7, where such handle 10 has sufficient leverage to enable the screw 1 to be turned rapidly and, consequently, pushed rapidly into a compost pile and to preclude the screw 1 from rotating as the screw 1 is withdrawn from the pile. Likewise, any powered device capable of producing rotary motion with sufficient torque to drill into the compost pile and with sufficient strength to prevent the screw from rotating during withdrawal from the compost pile could be utilized.

An additional option for the Compost Aerator and Monitor is having the second end 9 of the shaft 8—or the second end 5 of the screw 1 in an embodiment where there is no shaft—removably, rather than permanently, attached to either the traditional brace 6 or the simple handle 10. This is accomplished by having an adjustable aperture 11 on the brace 6 or handle 10, which adjustable aperture 11 is well known in the art, and shaping the second end of the shaft 7—as shown in FIG. 2, FIG. 4, FIG. 6, and FIG. 8—in the form which is traditionally used for removable insertion into the adjustable aperture of a brace.

Figure 9:
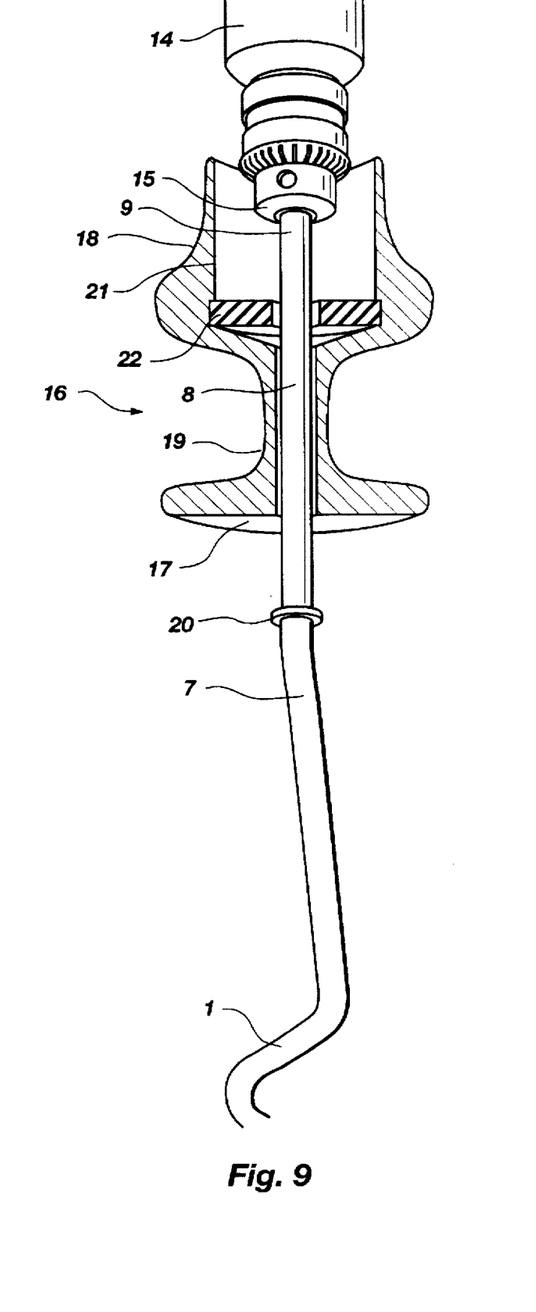
FIG. 9 illustrates an embodiment in which the shaft is removably inserted into a traditional power drill and where a guard is slidably mounted on the shaft.

In still another embodiment of the Compost Aerator and Monitor, depicted in FIG. 9, the traditional brace 6 is replaced with a traditional power drill 14 into the chuck 15 of which power drill 14 the second end 9 of the shaft 8—or the second end 5 of the screw 1 in an embodiment where there is no shaft—is removably inserted. With the power drill, it is preferable to utilize the shaft 8 and to have a guard 16 slidably mounted on such shaft 8.

The first end 17 of the guard 16 preferably is generally disc-shaped to prevent the guard 16 and, consequently, the chuck 15 of the power drill 14 from entering the compost. The guard 16 also protects the chuck 15 from striking any debris that may be near the surface of the compost pile.

Figure 10:
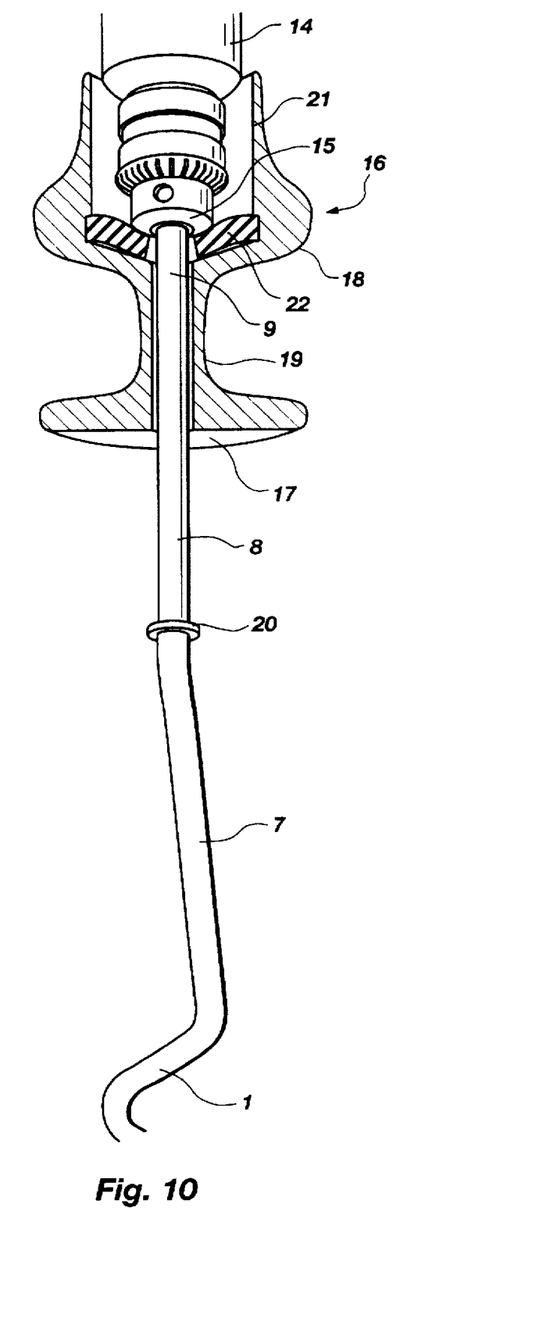
FIG. 10 shows the embodiment of FIG. 9 when the guard has been pulled against the power drill.

The second end 18 of the guard 16 preferably has a generally conical shape to permit the guard 16 to be removably pulled over the chuck 15 of the power drill 14, as illustrated in FIG. 10.

And between the first end 17 and the second 18 end of the guard 16 is the middle section 19 of the guard 16, which preferably has a cross-sectional diameter that is conveniently sized for grasping by a hand of a user.

When utilized with the power drill 14, the shaft 8 preferably has a stop 20 between the first end 7 and the second end 9 of the shaft 8 to preclude the guard 16 from reaching the screw 1.

Additionally, on the inside 21 of the guard 16 a pliable, high-friction insert 22, which is preferably composed of rubber, is placed so that it will be in contact with the chuck 15 when the guard 16 is pulled over the chuck 15 and against the power drill 14.

The method of using the Compost Aerator and Monitor is quite simple.

Figure 11:
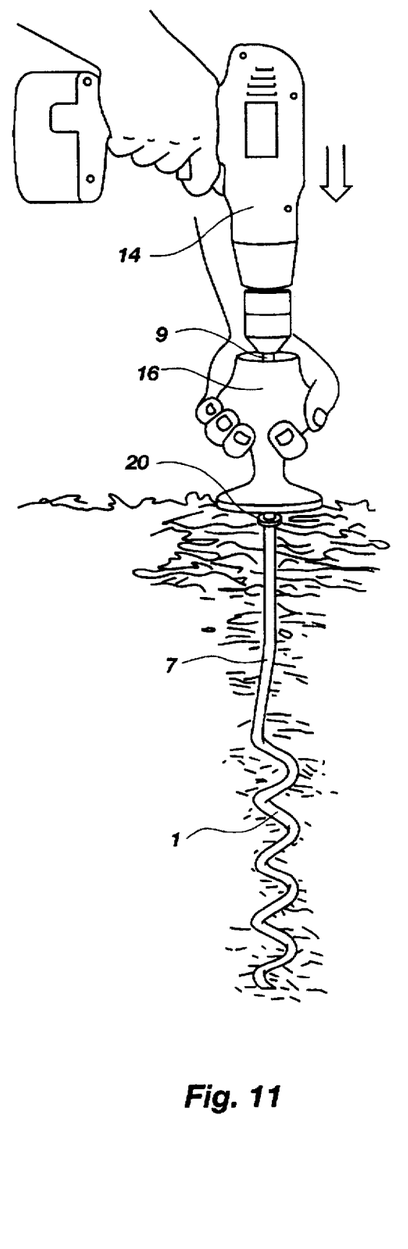
FIG. 11 demonstrates the embodiment of FIG. 9 at the completion of the process for inserting the screw into a compost pile.
Figure 12:
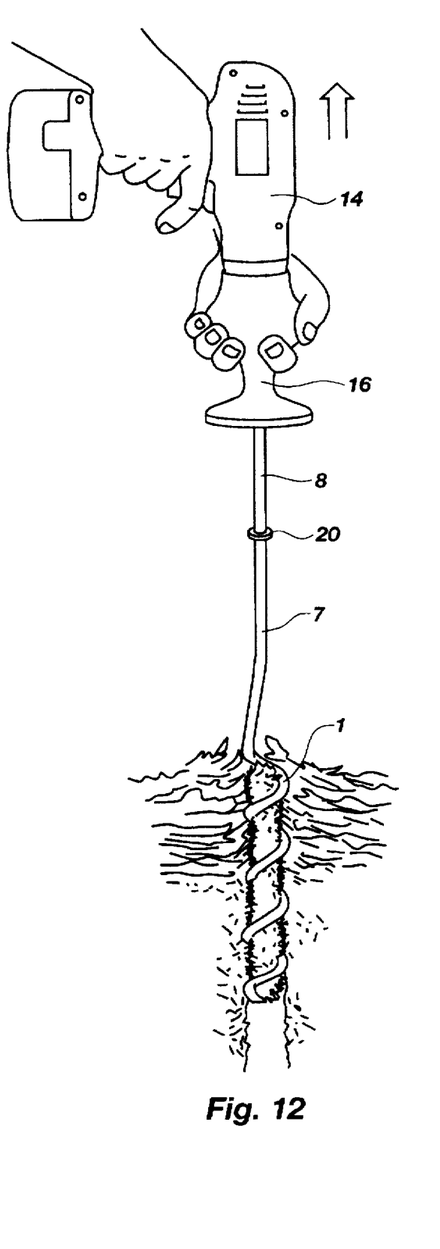
FIG. 12 shows the embodiment of FIG. 9 as the screw is withdrawn from the compost pile.

The handle 10 or brace 6 is merely rotated or the power drill 14 is activated to initiate rotation of the chuck 15, i.e., the portion of the power drill 14 that is removably connected to the shaft 8, which causes the screw 1 and, if rotation is continued long enough, the shaft 8 of the Compost Aerator and Monitor to penetrate the compost pile to a desired depth, as illustrated in FIG. 11. The Compost Aerator and Monitor is then pulled in the direction opposite to the direction in which the screw entered the compost pile while the handle 10 or the brace 6 is held or, in the embodiment with the power drill 14, the guard 16 is pulled against the chuck 15 of the power drill 14 with sufficient force—considering the leverage created by the handle 10 or the brace 6 or the friction produced by the pliable, high-friction insert 22—that the screw 1 does not rotate. This process, as depicted in FIG. 12, creates a cohesive, representative, cylindrical core of compost material within the screw 1 which may be utilized for analysis and, also, leaves a hole in the compost pile which facilitates the introduction of water as well as oxygen into the compost.

If the core of compost retained within the Compost Aerator and Monitor after the preceding process is not removed for analysis, subsequent reutilization of the Compost Aerator and Monitor will force the core from the device, leaving the material from the core on top of the compost pile where it mixes with newer material, which—as observed above—is generally located higher on the compost pile, and thereby accelerates the decay of such newer material.

This self-cleaning action also prevents newer material from being pushed lower where it would contaminate the underlying material that may have already reached the desired state of decomposition. Therefore, unlike the situation with traditional methods of mixing and turning the compost, higher layers can be scraped away to reveal compost that may then be removed and used as an organic fertilizer; after traditional mixing and turning, the entire quantity of disturbed material must be allowed to remain a sufficient length of time for the decomposition of the newly added material.

The guard 16, in addition to precluding rotation of the screw 1 during withdrawal of the screw 1 from a compost pile, preventing compost from entering the chuck 15 of the power drill 14, and keeping the chuck 15 from striking any debris, serves two other functions. This guard 16 may be grasped by the user to stabilize the screw 1 while it enters the compost pile; and then the guard 16, also, simultaneously protects the hand utilized by the user to stabilize the screw 1, from the rotating chuck 15.

I claim:

1. A compost aerator and monitor, which comprises:
    a screw shaped as a cylindrical helix, wherein the diameter of the central cylindrical cavity formed by the cylindrical helix of the screw and the tightness of the windings of the screw are of such sizes that, when the screw is inserted into a compost pile, there is collected within the windings of the screw a core of compost material that is sufficiently large to be cohesive and representative but not so large that the weight of the core will cause the core to fall from the screw when said screw is withdrawn from the compost pile.

2. The compost aerator and monitor as recited in claim 1, wherein:

a tip of a first end of said screw is sharpened.

3. The compost aerator and monitor as recited in claim 1, further comprising:

a brace attached to a second end of the screw.

4. The compost aerator and monitor as recited in claim 3, wherein:

a tip of a first end of said screw is sharpened.

5. The compost aerator and monitor as recited in claim 3, further comprising:

a shaft inserted between the brace and the second end of the screw, a first end of which shaft is attached to the second end of the screw and a second end of which shaft is attached to the brace.

6. The compost aerator and monitor as recited in claim 5, wherein:

a tip of a first end of said screw is sharpened.

7. The compost aerator and monitor as recited in claim 1, further comprising:

a handle attached to a second end of the screw.

8. The compost aerator and monitor as recited in claim 7, wherein:

a tip of a first end of said screw is sharpened.

9. The compost aerator and monitor as recited in claim 7, further comprising:

a shaft inserted between the handle and the second end of the screw, a first end of which shaft is attached to the second end of the screw and second end of which shaft is attached to the handle.

10. The compost aerator and monitor as recited in claim 9, wherein:

a tip of a first end of said screw is sharpened.

11. The compost aerator and monitor as recited in claim 1, further comprising:

a brace removably attached to a second end of the screw.

12. The compost aerator and monitor as recited in claim 11, wherein:

a tip of a first end of said screw is sharpened.

13. The compost aerator and monitor as recited in claim 11, further comprising:

a shaft inserted between the brace and the second end of the screw, a first end of which shaft is attached to the second end of the screw and a second end of which shaft is removably attached to the brace.

14. The compost aerator and monitor as recited in claim 13, wherein:

a tip of a first end of said screw is sharpened.

15. The compost aerator and monitor as recited in claim 1, further comprising:

a handle removably attached to a second end of the screw.

16. The compost aerator and monitor as recited in claim 15, wherein:

a tip of a first end of said screw is sharpened.

17. The compost aerator and monitor as recited in claim 15, further comprising:

a shaft inserted between the handle and the second end of the screw, a first end of which shaft is attached to the second end of the screw and a second end of which shaft is removably attached to the handle.

18. The compost aerator and monitor as recited in claim 17, wherein:

a tip of a first end of said screw is sharpened.

19. The compost aerator and monitor as recited in claim 1, further comprising:

a power drill removably attached to a second end of the screw.

20. The compost aerator and monitor as recited in claim 19, wherein:

a tip of a first end of said screw is sharpened.

21. The compost aerator and monitor as recited in claim 19, further comprising:

a shaft inserted between the power drill and the second end of the screw, a first end of which shaft is attached to the second end of the screw and a second end of which shaft is removably attached to the power drill.

22. The compost aerator and monitor as recited in claim 21, wherein:

a tip of a first end of said screw is sharpened.

23. The compost aerator and monitor as recited in claim 21, further comprising:

a guard slidably mounted on said shaft, such guard having placed inside the guard a pliable, high-friction insert in such a position that the pliable, high-friction insert will be in contact with a chuck of the power drill when the guard is pulled against the power drill.

24. The compost aerator and monitor as recited in claim 23, wherein:

a tip of a first end of said screw is sharpened.

25. A process for aerating and monitoring a compost pile, which comprises:

rotating a brace attached to a second end of a shaft, a first end of which shaft is attached to a second end of a screw, which screw is shaped as a cylindrical helix, wherein the diameter of the central cylindrical cavity formed by the cylindrical helix of the screw and the tightness of the windings of the screw are of such sizes that, when the screw is inserted into a compost pile, there is collected within the windings of the screw a core of compost material that is sufficiently large to be cohesive and representative but not so large that the weight of the core will cause the core to fall from the screw when said screw is withdrawn from the compost pile;

continuing such rotation, which causes the screw to be driven into the compost pile, until the screw has reached a desired depth; and then pulling the brace in the direction opposite to the direction in which the screw entered the compost pile while the brace is held with sufficient force, considering the leverage created by the brace, that the screw does not rotate.

26. A process for aerating and monitoring a compost pile, which comprises:

rotating a handle attached to a second end of a shaft, a first end of which shaft is attached to a second end of a screw, which screw is shaped as a cylindrical helix, wherein the diameter of the central cylindrical cavity formed by the cylindrical helix of the screw and the tightness of the windings of the screw are of such sizes that, when the screw is inserted into a compost pile, there is collected within the windings of the screw a core of compost material that is sufficiently large to be cohesive and representative but not so large that the weight of the core will cause the core to fall from the screw when said screw is withdrawn from the compost pile;

continuing such rotation, which causes the screw to be driven into the compost pile, until the screw has reached a desired depth; and then pulling the handle in the direction opposite to the direction in which the screw entered the compost pile while the handle is held with sufficient force, considering the leverage created by the handle, that the screw does not rotate.

27. A process for aerating and monitoring a compost pile, which comprises:

activating a power drill to initiate rotation of a chuck of said power drill, which chuck is removably connected to a second end of a shaft, a first end of which shaft is attached to a second end of a screw, which screw is shaped as a cylindrical helix, wherein the diameter of the central cylindrical cavity formed by the cylindrical helix of the screw and the tightness of the windings of the screw are of such sizes that, when the screw is inserted into a compost pile, there is collected within the windings of the screw a core of compost material that is sufficiently large to be cohesive and representative but not so large that the weight of the core will cause the core to fall from the screw when said screw is withdrawn from the compost pile;

continuing such rotation, which causes the screw to be driven into the compost pile, until the screw has reached a desired depth; and then pulling the power drill in a direction opposite to the direction in which the screw entered the compost pile while also pulling a guard against the power drill, which guard is slidably mounted on the shaft and which guard has a pliable, high-friction insert on the inside of the guard in a position so that it will be in contact with the chuck when the guard is pulled against the power drill, with sufficient force that the chuck and, therefore, the screw do not rotate as the screw is withdrawn from the compost pile.

* * * * *